United States Patent
Xu et al.

(10) Patent No.: US 10,762,631 B2
(45) Date of Patent: Sep. 1, 2020

(54) APPARATUS AND METHOD FOR CHARACTERIZING A TISSUE OF A SUBJECT

(71) Applicant: KONINKLIJKE PHILIPS N.V., Eindhoven (NL)

(72) Inventors: Jingping Xu, Shanghai (CN); Yinhui Deng, Shanghai (CN); Xiaomin Li, Shanghai (CN); Ying Wu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 134 days.

(21) Appl. No.: 16/063,309

(22) PCT Filed: Dec. 16, 2016

(86) PCT No.: PCT/EP2016/081563
§ 371 (c)(1),
(2) Date: Jun. 18, 2018

(87) PCT Pub. No.: WO2017/103196
PCT Pub. Date: Jun. 22, 2017

(65) Prior Publication Data
US 2019/0005645 A1    Jan. 3, 2019

(30) Foreign Application Priority Data

Dec. 18, 2015 (WO) ................. PCT/CN2015/097817
Jan. 27, 2016 (EP) ..................................... 16152888

(51) Int. Cl.
G06K 9/62       (2006.01)
G06T 7/00       (2017.01)
(Continued)

(52) U.S. Cl.
CPC ............. *G06T 7/0014* (2013.01); *A61B 8/085* (2013.01); *A61B 8/4416* (2013.01); *A61B 8/481* (2013.01);
(Continued)

(58) Field of Classification Search
CPC ....... A61B 8/085; A61B 8/4416; A61B 8/481; A61B 8/52; A61B 8/5207; G06T 7/0014; G06T 2207/10132; G06K 9/6202
(Continued)

(56) References Cited

U.S. PATENT DOCUMENTS 5,997,479 A    12/1999  Savord et al.
6,013,032 A     1/2000  Savord
(Continued)

FOREIGN PATENT DOCUMENTS

JP       2003245360 A    9/2003
JP       2009089736 A    4/2009
(Continued)

OTHER PUBLICATIONS

A. Jemal, et.al., 'Global cancer statistics', CA Cancer J Clin, 2011, vol. 61:69-90.
(Continued)

*Primary Examiner* — Ali Bayat

(57) ABSTRACT

The present invention proposes an apparatus and method for characterizing a tissue in a first region of a subject. The apparatus comprises a receiving unit (210) for receiving ultrasound data of the tissue in the first region and ultrasound data of a predetermined target reference tissue of said subject; a deriving unit (220) for deriving a subject-specific model of the target reference tissue on the basis of the ultrasound data of the target reference tissue; and a characterizing unit (230) for determining a match between tissue in the first region and the target reference tissue on the basis of
(Continued)

the subject-specific model and ultrasound data of the tissue in the first region. Unlike conventional tissue characterization based on a large cohort of patient data, the proposed subject-specific model is personalized for the specific subject without any generalization, resulting in higher sensitivity and/or accuracy. Preferably, the subject-specific model of the target reference tissue is derived on the basis of both the ultrasound data of the target reference tissue and the ultrasound data of a background reference tissue of a different type than the target reference tissue.

16 Claims, 3 Drawing Sheets

(51) Int. Cl.
    *A61B 8/08*     (2006.01)
    *A61B 8/00*     (2006.01)

(52) U.S. Cl.
    CPC ............... *A61B 8/488* (2013.01); *A61B 8/52* (2013.01); *A61B 8/5207* (2013.01); *G06K 9/6202* (2013.01); *G06T 2207/10132* (2013.01)

(58) Field of Classification Search
    USPC .......................................................... 382/209
    See application file for complete search history.

(56) References Cited

U.S. PATENT DOCUMENTS

| | | | |
|---|---|---|---|
| 6,283,919 B1 | 9/2001 | Roundhill et al. | |
| 6,458,083 B1 | 10/2002 | Jago et al. | |
| 6,623,432 B2 | 9/2003 | Powers et al. | |
| 2001/0051774 A1* | 12/2001 | Littrup | A61B 5/053 600/547 |
| 2004/0059216 A1 | 3/2004 | Vetter et al. | |
| 2014/0046172 A1* | 2/2014 | Kim | A61B 5/7275 600/411 |
| 2014/0288424 A1* | 9/2014 | Mukdadi | A61B 8/403 600/438 |
| 2014/0369584 A1 | 12/2014 | Fan et al. | |
| 2016/0231322 A1* | 8/2016 | Smith | G01N 33/6872 |
| 2016/0256135 A1* | 9/2016 | Susumu | A61B 8/485 |
| 2016/0312295 A1* | 10/2016 | Ayers | C07K 16/2818 |
| 2018/0181705 A1* | 6/2018 | Kilpinen | G06F 16/2457 |

FOREIGN PATENT DOCUMENTS

| | | |
|---|---|---|
| WO | 2014139021 A1 | 9/2014 |
| WO | 2014162232 A1 | 10/2014 |

OTHER PUBLICATIONS

A. C. Fleischer, et. al., 'Sonographic depiction of micro-vessel perfusion', Journal Ultrasound Medicine, 2004, vol. 23: 1499-1506.
D. Beggs and P. R.S. Thomas, 'Point of use ultrasound by general surgeons: Review of the literature and suggestions for future practice', International Journal of Surgery, 2013, vol. 11: 12-17.
L. Drudi, et.al., 'Surgery in space: where are we at now?', Acta Atronaut, 2012, vol. 79: 61-66.
M. Garancini, et. al., Chapter 8: The role of ultrasound in hepatic surgery, InTech, 2013 (http://www.intechopen.com/books/hepatic-surgery.

\* cited by examiner

APPARATUS AND METHOD FOR CHARACTERIZING A TISSUE OF A SUBJECT

This application is the U.S. National Phase application under 35 U.S.C. § 371 of International Application No. PCT/EP2016/081563, filed on Dec. 16, 2016, which claims the benefit of Application Serial No. PCT/CN2015/097817, filed Dec. 18, 2015 and EP 16152888.0 filed Jan. 27, 2016. These applications are hereby incorporated by reference herein.

FIELD OF THE INVENTION

The present invention relates to an apparatus and method for characterizing a tissue of a subject, and more particularly to an apparatus and method for characterizing a tissue of a subject on the basis of a subject-specific model derived from ultrasound data of a target reference tissue.

BACKGROUND OF THE INVENTION

Medical imaging technologies such as CT, MRI and Ultrasound are widely used in the detection of abnormal tissue such as tumors. There are various types of abnormal tissue. For example, tumors in the same organ can be benign or malignant.

Ultrasound is especially suitable for immediate assessment pre or post tumor resection before closing the chest in the surgery. In the case of a liver tumor, for example, before and/or after resecting the tumor identified, the surgeon may use intraoperative ultrasound (IOUS) to search the whole liver to identify any undetected suspicious small tumor (for example: diameter less than 5 mm) which has been previously missed by conventional trans-abdominal ultrasound examination, or a residual tumor. In comparison with trans-abdominal ultrasound, IOUS has several advantages, including: IOUS does not suffer from the acoustic attenuation caused by the abdominal wall and thus may utilize a higher frequency to obtain a higher spatial resolution; the liver has to be "spied" on within the acoustic windows (e.g. trans-costal) in the trans-abdominal ultrasound, whilst the IOUS probe can be placed in contact with the anterior, superior, inferior or posterior liver surface and the tissue of interest can be studied from different points of view; during IOUS, information obtained by means of the ultrasound and information obtained by inspection and palpation can complement each other.

However, IOUS has the same drawback as trans-abdominal ultrasound, namely that visual observations of ultrasound images are highly dependent on an operator's experience. Surgeons are often not equipped with the same level of ultrasound skills as their surgical skills. In practice, ultrasound doctors with sophisticated ultrasound skills are often asked by surgeons to come to the operating room to evaluate the ultrasound images. Even for ultrasound doctors, the evaluation of ultrasound images is not easy due to the limited time available for IOUS. Therefore, highly specialized training is required for this task. Even so, the evaluation results are operator-dependent.

U.S. 2014/0288424 A1 discloses a method and a device to image and characterize human tumors, ad to classify the tumors as either malignant or benign. The method includes using a multi-compression technique upon the tissue or organ combined with a 3 ultrasound strain imaging of the compressed tissue or organ for acquiring raw data and analyzing the raw data using a computer processing unit equipped with a nonlinear biomechanical tissue model for tumor classification.

SUMMARY OF THE INVENTION

Therefore, it would be advantageous to provide an improved ultrasound system and method for characterizing tissue of a subject.

The inventors of the present invention recognize that the conventional tissue characterization has the following disadvantages. The conventional tissue characterization for both tumor and normal liver is based on a large cohort of patient data. A machine learning approach is often performed to learn the model which is supposed to distinguish between tumor tissue and normal liver tissue for all the patients. Consequently, a generalization of the model is expected. However, some person's "normal" tissue might be considered as "abnormal" or "diseased" tissue for other persons, e.g. a cirrhosis patient. For example, a normal tissue of a cirrhosis patient could be mistakenly characterized as an abnormal tissue on the basis of the generalized model. Thus, the sensitivity and/or the accuracy of the conventional tissue characterization is restricted by such generalization of the model.

Therefore, it would be advantageous to provide an improved ultrasound system and method for characterizing a tissue of a subject.

In accordance with an embodiment of a first aspect of the present invention, there is proposed an apparatus for characterizing a tissue in a first region of a subject. The apparatus comprises: a receiving unit for receiving ultrasound data of the tissue in the first region and ultrasound data of a pre-determined target reference tissue of said subject; a deriving unit for deriving a subject-specific model of the target reference tissue on the basis of the ultrasound data of the target reference tissue; and a characterizing unit for determining a match between the tissue in the first region and the target reference tissue on the basis of the subject-specific model and ultrasound data of the tissue in the first region.

The subject-specific model is derived on the basis of ultrasound data of the specific subject itself, rather than ultrasound data of a large amount of subjects like in the conventional tissue characterization. Thus, the subject-specific model is personalized for the specific subject without any generalization, resulting in higher sensitivity and/or accuracy. The subject-specific model is used to identify a match between any tissue of the subject and the target reference tissue of the subject. The proposed tissue characterization is applicable for cases where certain tissue of the subject has been previously characterized, e.g. predetermined as a specific type of tissue such as an abnormal tissue, and it is an object to characterize other tissue of the same subject on basis of the predetermined tissue. In other words, the inventors of the present invention have proposed to utilize prior knowledge on the tissue characterization of a certain tissue of a subject, called target reference tissue herein, to build up a personalized tissue model and then use such personalized tissue model to characterize other tissue of the same subject, for example to search for tissue that is the same as or at least similar to the target reference tissue. The information on the similarity and/or match between the target reference tissue and the tissue to be characterized can assist the clinicians to evaluate the ultrasound data in a more efficient and/or operator-independent way.

Prior knowledge on the tissue characterization of the target reference tissue can be obtained in various ways. The tissue characterization of the target reference tissue can be achieved (1) by means of medical imaging modalities such as CT, MRI, ultrasound, (2) by means of manual inspection and palpation, and/or (3) by means of pathological procedures such as biopsy. The target reference tissue may still exist or not inside the subject when characterizing the tissue of the subject. In an example, a tumor, as the target reference tissue, may be first identified by means of medical imaging modalities on the basis of certain non-personalized models or by means of medical imaging modalities other than ultrasound, and the proposed tissue characterization is used to assist the clinicians to identify any additional tumor undetected by means of the ultrasound data based non-personalized model. In another example, a malignant lesion, as the target reference tissue, may be first identified by means of biopsy, and then the proposed tissue characterization is used to assist the clinicians to identify whether the other lesion of the same subject is malignant or benign. In another example, in a tumor resection surgery, the proposed tissue characterization is used to assist the clinicians to identify, after opening the chest, any residual tumor or additional tumor undetected/missed without opening the chest. In another example, the target reference target can be a tumor detected in the past, and may have been resected or cured, and then the subject is examined to detect whether there is a new tumor developing in a follow-up procedure.

In accordance with an embodiment, the characterizing unit can be configured to determine a score for indicating the match between the tissue and the target reference tissue.

In accordance with an embodiment, the target reference tissue is a first type of abnormal tissue.

In accordance with an embodiment, the receiving unit is further configured to receive ultrasound data of a background reference tissue of said subject, the background reference tissue being predetermined to be of a different type than the target reference tissue; and the deriving unit is further configured to derive the subject-specific reference model of the target tissue on the basis of the ultrasound data of the target reference tissue and the ultrasound data of the background reference tissue.

In this way, the subject-specific model is derived not only on the basis of the ultrasound data of the target reference tissue of the subject but also on basis of the ultrasound data of a background reference tissue of the subject which has been pre-determined to be of a different type than the target tissue. In other words, the proposed tissue characterization further utilizes the prior knowledge of certain tissue, called background reference tissue herein, of the subject being of a different type than the target reference tissue to build up the personalized tissue model (i.e. the subject-specific model) for the target reference tissue. Thus, the subject-specific model can model the target reference tissue, or in other words cause the target reference tissue model to differ from the background reference tissue model in a better way. Consequently, the sensitivity and/or accuracy of using the subject-specific model to identify tissues of the same type as the target reference tissue can be further improved. A higher match between the tissue and the target reference tissue also indicates a lower match between the tissue and the background reference tissue.

In accordance with an embodiment, the background tissue is a type of normal tissue or a second type of abnormal tissue, and the second type of abnormal tissue is different from the first type of abnormal tissue.

In accordance with an embodiment, ultrasound data of more than one background reference tissues can be used to derive the subject-specific model. For example, the subject-model of a liver tumor can be derived on the basis of the ultrasound data of a pre-determined liver tumor as the target reference tissue, or on the basis of the ultrasound data of both a pre-determined liver normal tissue and a pre-determined liver cirrhosis tissue as background reference tissues.

In accordance with an embodiment, in case there is more than one predetermined target tissue, such as more than one predetermined tumor, the subject-model can be derived on the basis of the ultrasound data of the more than one predetermined target tissue.

In accordance with an embodiment, the receiving unit is further configured to receive ultrasound data of a second region of said subject, the second region comprising the target reference tissue; to receive position information indicative of a position of the target in the second region; and to extract the ultrasound data of the target reference tissue from the received ultrasound data of the second region and the received position information.

In accordance with an embodiment, the receiving unit is further configured to receive ultrasound data of the first region, the first region comprising a plurality of tissue units; and the characterizing unit is further configured to determine, for each of the plurality of tissue units, a match between the tissue unit and the target reference tissue on the basis of the subject-specific model and the ultrasound data of the tissue unit.

In accordance with an embodiment, the subject-specific model of the target tissue comprises specified ranges for a set of features derived from the ultrasound data of the target reference tissue.

The set of features can be a predetermined set of features, or can be a set of features automatically generated by means of machine learning in the course of the derivation of the subject-specific model.

In accordance with an embodiment of a second aspect of the present invention, there is proposed an ultrasound system. The ultrasound system comprises the aforementioned apparatus for characterizing a tissue in a first region of a subject; and an ultrasound probe for acquiring the ultrasound data of the tissue in the first region and ultrasound data of a predetermined target reference tissue of said subject, and transmitting the acquired ultrasound data to the aforementioned apparatus.

In accordance with an embodiment, the ultrasound probe can be a trans-abdominal ultrasound probe, or can be an intra-operative ultrasound probe.

In accordance with an embodiment, the ultrasound system further comprises a user interface, wherein the characterizing unit is further configured to generate an indicator for indicating the match between the tissue and the target reference tissue; and the user interface is configured to present the generated indicator to a user.

In accordance with an embodiment of a third aspect of the present invention, there is proposed a method of characterizing a tissue in a first region of a subject. The method comprises: receiving ultrasound data of the tissue in the first region and ultrasound data of a pre-determined target reference tissue of said subject; deriving a subject-specific model of the target reference tissue on the basis of the ultrasound data of the target reference tissue; and determining a score for indicating the match between the tissue in the first region and the target reference tissue on the basis of the subject-specific model and ultrasound data of the tissue in the first region.

In accordance with an embodiment, the method further comprises: acquiring, via an ultrasound probe, the ultrasound data of the tissue in the first region and the ultrasound data of the target reference tissue.

In accordance with an embodiment, the method further comprises: receiving ultrasound data of a background reference tissue of said subject, the background reference tissue being predetermined to be of a different type than the target reference tissue; and deriving the subject-specific reference model of the target tissue type on the basis of the ultrasound data of the target reference tissue and the ultrasound data of the background reference tissue.

In accordance with an embodiment, the method further comprises: acquiring, via the ultrasound probe, the ultrasound data of the target reference tissue of said subject prior to the target reference tissue being removed from said subject; and acquiring, via the ultrasound probe, the ultrasound data of the tissue in the first region of said subject after the target reference tissue being removed from said subject.

The removal of the target reference tissue can be the resection of the target reference tissue, or can be any suitable treatment for the target reference tissue which changes the type and/or property of the target reference tissue.

In accordance with an embodiment of a fourth aspect of the present invention, there is proposed a computer program, comprising computer program instructions, which, when being executed, performs the aforementioned method of characterizing a tissue in a first region of a subject.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein.

Figure 1:
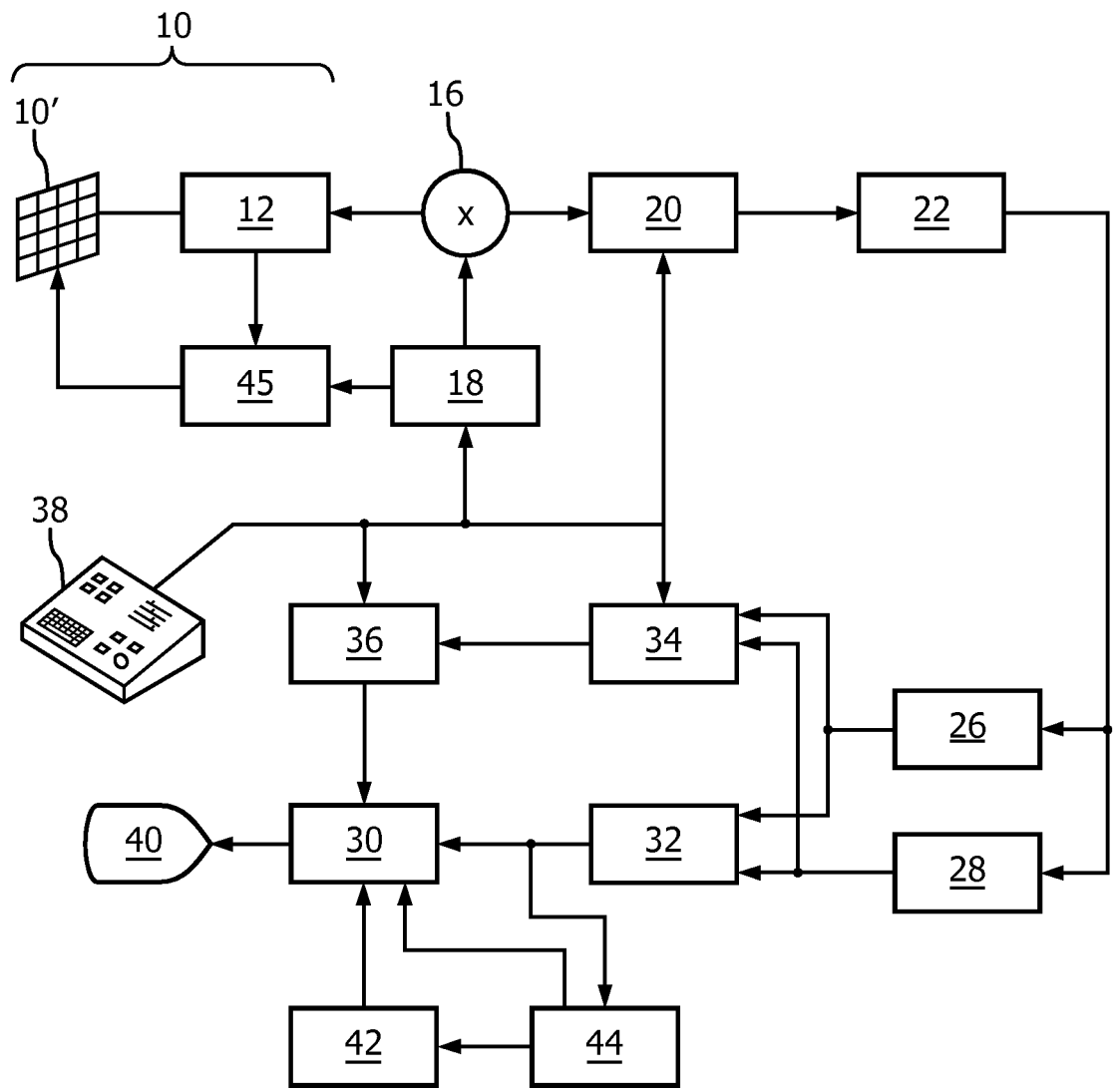
FIG. 1 illustrates, in a block diagram form, an ultrasound imaging system constructed in accordance with some embodiments of the present invention.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

Referring first to FIG. 1, an ultrasound system constructed in accordance with some embodiments of the present invention is shown in block diagram form.

Referring first to FIG. 1, an ultrasonic system with an array transducer probe is shown in block diagram form. In FIG. 1, an ultrasound probe (for example: a CMUT transducer array 10') is provided in 10 for transmitting ultrasonic waves and receiving echo information. The transducer array 10' may alternatively comprise piezoelectric transducer elements formed of materials such as PZT or PVDF. The transducer array 10' is a one- or two-dimensional array of transducer elements capable of scanning in a 2D plane or in three dimensions for 3D imaging. The transducer array is coupled to a microbeam former 12 in the probe which controls transmission and reception of signals by the CMUT array cells or piezoelectric elements. Microbeam formers are capable of at least partial beam forming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeam former is coupled by the probe cable to a transmit/receive (T/R) switch 16 which switches between transmission and reception and protects the main beam former 20 from high energy transmit signals when a microbeam former is not used and the transducer array is operated directly by the main system beam former. The transmission of ultrasonic beams from the transducer array 10 under control of the microbeam former 12 is directed by a transducer controller 18 coupled to the microbeam former by the T/R switch and the main system beam former 20, which receives input from the user's operation of the user interface or control panel 38. One of the functions controlled by the transducer controller is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets one or more DC bias voltages that are applied to the CMUT cells.

The partially beam-formed signals produced by the microbeam former 12, on receive, are coupled to a main beam former 20 where partially beam formed signals from individual patches of transducer elements are combined into a fully beam formed signal. For example, the main beam former 20 may have 128 channels, each of which receives a partially beam-formed signal from a patch of dozens or hundreds of CMUT transducer cells or piezoelectric elements. In this way, the signals received by thousands of transducer elements of a transducer array can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles if working in the contrast-enhanced ultrasound (CEUS) mode. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 26 and a Doppler processor 28. The B mode processor 26 employs detection of an amplitude of the received ultrasound signal for the imaging of structures in the body such as the tissue of organs and vessels in the body. B mode images of structures of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signals of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point being referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multiplanar reformatter 44. The volume renderer 42 is coupled to an image processor 30 for further enhancement, buffering and temporary storage for display on an image display 40.

Alternatively or additionally to being used for imaging, the blood flow values produced by the Doppler processor 28 and tissue structure information produced by the B mode processor 26 are coupled to a quantification processor 34. Optionally, the quantification processor may receive input from the user control panel 38, such as the point in the anatomy of an image where a measurement is to be made. Output data from the quantification processor can be coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like.

Alternatively or additionally to the B mode processor 26 and the Doppler processor 28, the processed signals are coupled to a processor for performing other ultrasound modalities such as M-mode, strain mode, etc.

The skilled person in the art would appreciate that the scan converter 32, the multiplanar reformatter 44, volume renderer 42, image processor 30 can be omitted in some embodiments if no ultrasound image is to be displayed.

In accordance with an embodiment of the present invention, the ultrasound probe 10 is configured to acquire ultrasound data of the tissue in the first region of a subject and ultrasound data of a predetermined target reference tissue of the same subject. The ultrasound probe can be a transabdominal ultrasound probe or can be an intraoperative ultrasound (IOUS) probe. The quantification processor 32 is configured to characterize the tissue in the first region on the basis of the acquired ultrasound data. The quantification processor comprises a receiving unit for receiving ultrasound data of the tissue in the first region and ultrasound data of a pre-determined target reference tissue of said subject; a deriving unit for deriving a subject-specific model of the target reference tissue on the basis of the ultrasound data of the target reference tissue; and a characterizing unit for determining a match between tissue in the first region and the target reference tissue on the basis of the subject-specific model and ultrasound data of the tissue in the first region. In other words, the quantification processor 32 acts as the apparatus 200 of FIG. 2. In some other embodiments, the apparatus 200 of FIG. 2 can be a separate device from an ultrasound system.

Figure 2:
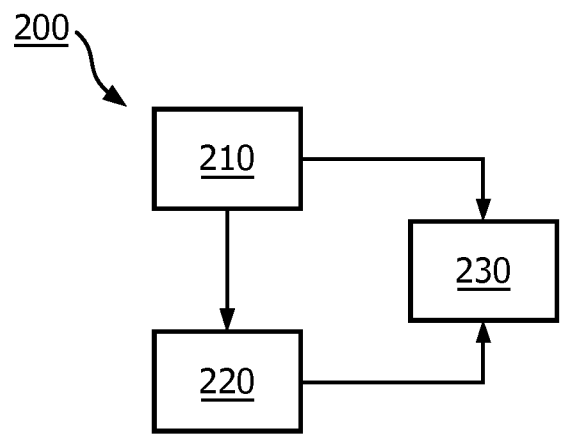
FIG. 2 illustrates an apparatus for characterizing a tissue in a first region of a subject in accordance with some embodiments of the present invention.

FIG. 2 illustrates an apparatus 200 for characterizing a tissue in a first region of a subject in accordance with some embodiments of the present invention. Referring to FIG. 2, the apparatus 200 comprises a receiving unit 210, a deriving unit 220 and a characterizing unit 230.

The receiving unit 210 is configured to receive ultrasound data of the tissue to be characterized in the first region of the subject and ultrasound data of a predetermined target reference tissue of the subject.

By pre-determined target reference tissue is meant that certain tissue is predetermined as a target type, such as tumor, malignant lesion, etc., and is called target reference tissue. The subject can be a human such as a patient, or an animal etc. The first region can be two dimensional or three dimensional. The ultrasound data can comprise data of one or more ultrasound modalities, including but not limited to B-mode, Doppler-mode, contrast-enhanced ultrasound (CEUS), strain and or elasticity mode (called E-mode later). The ultrasound data can be processed data such as ultrasound images and or image sequences, or can be raw RF ultrasound data.

The receiving unit 210 can receive the ultrasound data from an ultrasound probe, or can receive the ultrasound data from any other system or database. The ultrasound data may be of DICOM format.

The receiving unit 210 can receive the ultrasound data of the tissue to be characterized in the first region in various ways. For example, the receiving unit 210 is configured to receive the ultrasound data of the first region, and to extract the ultrasound data of the tissue to be characterized from the received ultrasound data. In an embodiment, the tissue to be characterized is set by the user on an ultrasound image via a user interface. In another embodiment, the receiving unit 210 is configured to receive ultrasound data of the first region. The first region comprises a plurality of tissue units. Each of the plurality of tissue units can comprise one or more pixels in case of 2D data or one or more voxels in case of 3D data. Each tissue unit is regarded as a tissue to be characterized. In an embodiment, the user sets a region of interest on an ultrasound image as the first region. Alternatively, the overall region of an ultrasound image is set as the first region. In other words, each tissue unit in the ultrasound image is to be characterized.

The receiving unit 210 can receive the ultrasound data of the target reference tissue in various ways. In some embodiments, the receiving unit 210 is configured to directly receive the ultrasound data of the target reference tissue. In some other embodiments, the receiving unit 210 is configured to receive ultrasound data of a second region of said subject comprising the target reference tissue, to receive position information indicative of a position of the target in the second region, and to extract the ultrasound data of the target reference tissue from the received ultrasound data of the second region and the received position information.

The position information can comprise information indicative of the boundary of the target reference tissue, or can comprise information indicative of the center position and the size of the target reference tissue.

The position information may be received in various ways. In an embodiment, the position information can be generated on the basis of a user input via a user interface and then provided to the receiving unit. For example, the surgeon can indicate the position of the target reference tissue in the ultrasound image of the second region. In another embodiment, the target reference tissue has been pre-determined in a CT/MRI image, and the position of the target reference tissue in the ultrasound image of the second region can be determined on the basis of the position of the target reference tissue in the CT/MRI image and the registration between the CT/MRI image and the ultrasound image of the second region. For example, the receiving unit 210 receives images from previous CT, MRI or ultrasound examinations together with diagnostic information. The diagnostic information can comprise the size of a target reference tissue such as a tumor, the position of the target reference tissue and/or properties of the target reference tissue.

The second region and the first region can be the same or different. For example, in case of detecting residual tumor, the second region and the first region can be the same region where the tumor locates; in case of detecting undetected/missed tumor in the liver, the second region can cover the whole liver whilst the first region is where the pre-determined tumor locates.

In some embodiments, the receiving unit 210 is further configured to receive ultrasound data of a background reference tissue of said subject. The background reference tissue is pre-determined to be of a different type than the target reference tissue.

The target reference tissue is a first type of abnormal tissue. The background reference tissue is a type of normal tissue or a second type of abnormal tissue. In an example, the target reference tissue is a liver tumor, and the background reference tissue is a normal liver tissue. In another example, the target reference tissue is a liver tumor, and the background reference tissue is liver cirrhosis tissue. In another example, the target reference tissue is a malignant lesion, and the background reference tissue is a benign lesion.

The deriving unit 220 is configured to derive a subject-specific model of the target reference tissue on the basis of the ultrasound data of the target reference tissue. In some other embodiments, the deriving unit 220 is further configured to derive the subject-specific reference model of the target tissue on the basis of the ultrasound data of the target reference tissue and the ultrasound data of the background reference tissue.

The subject-specific model can be derived in any suitable existing or future-developed modeling technologies, including but not limited to clustering, Neural Networks, kernel method, Bayesian model, etc.

In some embodiments, the subject-specific model of the target tissue comprises specified ranges for a set of features derived from the ultrasound data of the target reference tissue. The set of features can comprise parameters for image properties (e.g., speckle stats, texture, etc.). For example, the features can be acoustic parameters (e.g., shadowing, speed of sound, attenuation), morphological parameters (e.g., lesion shape, border irregularity, etc.), and textural parameters such as first and second order speckle statistics (e.g., mean, median, skewness, kurtosis) or fractal dimension. Alternatively or additionally, the set of features can comprise parameters for properties of the raw received echo data. For example, the set of features can be the spectral characteristics and statistical moments of radiofrequency (RF) data, such as mean frequency, frequency dependence of attenuation, or integrated backscatter. Furthermore, the set of features can be acquired by means of various ultrasound modalities, including but not limited to B-mode, Doppler-mode, contrast-enhanced ultrasound (CEUS), strain mode.

The set of features can be a predetermined set of features, or can be a set of features automatically generated by means of machine learning without predefinition.

The characterizing unit 230 is configured to determine a match between tissue in the first region and the target reference tissue on the basis of the subject-specific model and ultrasound data of the tissue in the first region. In some embodiments, the characterizing unit 230 can determine an indicator for indicating the match between the tissue and the target reference tissue. For example, the indicator can be a score. In some embodiments, a user interface is provided to present the indicator.

Figure 3:
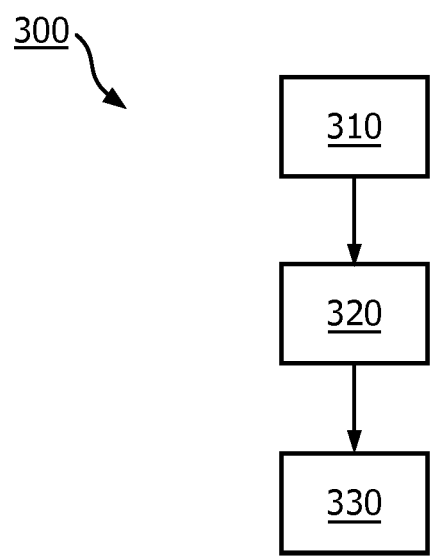
FIG. 3 illustrates a method of characterizing a tissue in a first region of a subject in accordance with some embodiments of the present invention.

FIG. 3 illustrates a method 300 of characterizing a tissue in a first region of a subject in accordance with some embodiments of the present invention.

In step 310, the ultrasound data of the tissue in the first region and ultrasound data of a pre-determined target reference tissue of said subject are obtained.

In step 320, a subject-specific model of the target reference tissue is derived on the basis of the ultrasound data of the target reference tissue.

In step 330, a match between tissue in the first region and the target reference tissue is determined on the basis of the subject-specific model and ultrasound data of the tissue in the first region.

In some other embodiments, the subject-specific model of the target reference tissue is derived on the basis of both the ultrasound data of the target reference tissue and the ultrasound data of a background reference tissue which is of a different type than the target reference tissue.

The skilled person would appreciate that the above steps 310 to 330 are not necessarily performed in the illustrated order, but can be performed in different orders in different embodiments. For example, the ultrasound data of the target reference tissue and the ultrasound data of the tissue to be characterized can be acquired in one medical examination, or can be acquired in different medical examinations carried out at a different date.

In the case of a post-evaluation of a tumor resection procedure for detecting suspected new tumors, the ultrasound data of the tissue to be characterized is acquired at the time of the post-evaluation procedure, the ultrasound data of the previously resected tumor as the target reference tissue can be acquired at the time of the former tumor resection procedure, and the ultrasound data of the background reference tissue can be acquired either at the time of the former tumor resection procedure or at the time of the post-evaluation procedure. The ultrasound probe can be a trans-abdominal ultrasound probe.

In the case of detecting a residual tumor or missed tumor in the tumor resection procedure, the surgeon may first open the patient's chest, and then use an IOUS probe to acquire the ultrasound of the tumor to be resected as the target reference tissue, and preferably the ultrasound data of a normal tissue as the background reference tissue. After the surgeon removes the tumor, the surgeon uses the IOUS probe again to scan the area adjacent to the resected tumor to see whether there is any residual tumor. In this case, each tissue unit in the area is to be characterized on basis of the subject-specific model. Alternatively or additionally, either before or after the removal of the predetermined tumor, the surgeon uses the IOUS probe to scan the whole organ to see whether there is any missed tumor, i.e. undetected prior to the procedure, or a newly developed tumor after the previous examination procedure.

In the case of detecting a malignant lesion among a number of detected lesions, the clinician may first detect at least one malignant lesion by means of a biopsy or surgical excision followed by histopathology or the like, and the at least one malignant lesion is used as the target reference tissue. Then, the ultrasound data of the at least one malignant lesion is collected and used to derive the subject-specific model for the malignant lesion. Then, the ultrasound data of remaining lesions are collected and the match between each of the remaining lesions and the subject-specific model is determined accordingly.

Figure 4:
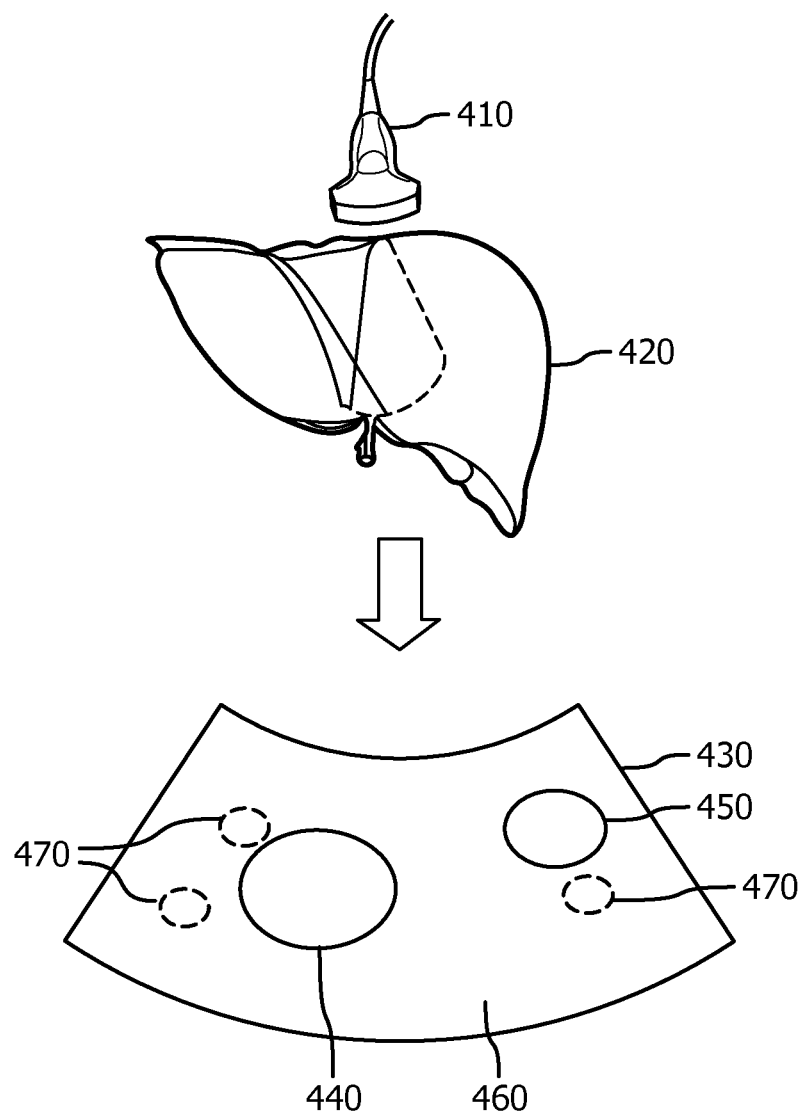
FIG. 4 illustrates an exemplary application of characterizing a tissue in a first region of a subject in accordance with an embodiment of the present invention.

FIG. 4 illustrates an exemplary application of characterizing a tissue in a first region of a subject in accordance with an embodiment of the present invention. In FIG. 4, liver tissues are characterized, but the skilled person would appreciate that the proposed tissue characterization can be applied to other organs as well. Referring to FIG. 4, an ultrasound probe 410 is used to scan the liver 420 of a subject. In the field of view 430 of the ultrasound probe 410, region 440 is a pre-detected tumor to be resected, region 450 is a pre-detected benign lesion to be left untreated kept, region 560 is normal background tissue or background tissue with diffused diseases such as fat liver, cirrhosis, hepato-fibrosis, regions 570 are missed tumors or newly developed tumors which have not been detected prior to performing the proposed tissue characterization. In this case, the ultrasound data of the tumor 440, the ultrasound data of the benign lesion 450, and the ultrasound data of the background tissue 560 are acquired to derive a subject-specific model for the tumor 440. Then, the whole liver region is scanned with the ultrasound probe to detect whether there is any tissue region having similar characteristics as the tumor 440. In particular, a match between the ultrasound data of each of one or more tissue regions and the derived subject-specific model is determined. In some embodiments, a pre-determined threshold or criterion can be used to determine the level of match. In case there is any tissue region that matches the subject-specific model, such a tissue region can be presented to the users for further procedure.

The technique processes described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. With software, implementation can be through modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture, using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the terms "beam former", "controller", "processor" such as quantification processor, "cross-correlator", "receiving unit", "deriving unit" and "characterizing unit" are intended to refer to a general-purpose processor, a specific-purpose processor, a computer processor, or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An apparatus for characterizing a tissue in a first region of a subject, the apparatus comprising:
   a receiving unit for receiving ultrasound data of the tissue in the first region, ultrasound data of a pre-determined target reference tissue of said subject, and ultrasound data of a background reference tissue of said subject, wherein the pre-determined target reference tissue is a different tissue type from the background tissue reference;
   a deriving unit for deriving a subject-specific model of the target reference tissue on the basis of the ultrasound data of the target reference tissue and ultrasound data of the background reference tissue; and
   a characterizing unit for determining a match between the tissue in the first region and the target reference tissue on the basis of the derived subject-specific model and ultrasound data of the tissue in the first region.

2. The apparatus of claim 1, wherein the target reference tissue is a first type of abnormal tissue.

3. The apparatus of claim 2, wherein the background reference tissue is a type of normal tissue or a second type of abnormal tissue, the second type of abnormal tissue being different than the first type of abnormal tissue.

4. The apparatus of claim 1, wherein the receiving unit is further configured to:
  receive ultrasound data of a second region of said subject, the second region comprising the target reference tissue;
  receive position information indicative of a position of the target in the second region; and
  extract the ultrasound data of the target reference tissue from the received ultrasound data of the second region and the received position information.

5. The apparatus of claim 1, wherein
  the receiving unit is further configured to receive ultrasound data of the first region, the first region comprising a plurality of tissue units; and
  the characterizing unit is further configured to determine, for each of the plurality of tissue units, a match between the tissue unit and the target reference tissue on the basis of the subject-specific model and the ultrasound data of the tissue unit.

6. The apparatus of claim 1, wherein the subject-specific model of the target tissue comprises specified ranges for a set of features derived from the ultrasound data of the target reference tissue.

7. The apparatus of claim 1, wherein the ultrasound data of the tissue in the first region is received from an ultrasound probe.

8. The apparatus of claim 7, wherein the ultrasound probe is an intra-operative ultrasound probe.

9. The ultrasound apparatus of claim 1, wherein the apparatus is configured to display the match on a user interface.

10. The apparatus of claim 1, wherein determining the match between tissue in the first region and the target reference tissue comprises determining a match between the ultrasound data of the tissue in the first region and the derived subject-specific model.

11. A method of characterizing a tissue in a first region of a subject, the method comprising:
  receiving ultrasound data of the tissue in the first region, ultrasound data of a pre-determined target reference tissue of said subject, and ultrasound data of a background reference issue of said subject, wherein the pre-determined target reference tissue is a different tissue type from the background tissue reference;
  deriving a subject-specific model of the target reference tissue on the basis of the ultrasound data of the target reference tissue and ultrasound data of background tissue reference; and
  determining a score for indicating a match between the ultrasound data of the tissue in the first region and the derived subject-specific model.

12. The method of claim 11, further comprising:
  acquiring, via the ultrasound probe, the ultrasound data of the target reference tissue of said subject prior to the target reference tissue being removed from said subject; and
  acquiring, via the ultrasound probe, the ultrasound data of the tissue in the first region of said subject after the target reference tissue being removed from said subject.

13. The method of claim 11, further comprising acquiring ultrasound data of the tissue in the first region via an ultrasound probe.

14. The method of claim 13, wherein the ultrasound probe is an intra-operative ultrasound probe.

15. The method of claim 11, wherein the target reference tissue is a first type of abnormal tissue.

16. The method of claim 15, wherein the background reference tissue is a type of normal tissue or a second type of abnormal tissue, the second type of abnormal tissue being different than the first type of abnormal tissue.

* * * * *